United States Patent [19]
Eugster et al.

[11] Patent Number: 5,593,691
[45] Date of Patent: Jan. 14, 1997

[54] BIOTENSIDE SOLVENTS FOR PHARMACEUTICALS AND COSMETICS

[75] Inventors: Carl Eugster, Riehen; Conrad H. Eugster, Wallisellen; Walter Haldemann, Binningen, all of Switzerland; Giorgio Rivara, Turin, Italy

[73] Assignee: Marigen S.A., Riehen, Switzerland

[21] Appl. No.: 179,729

[22] Filed: Jan. 11, 1994

[30]    Foreign Application Priority Data

Jun. 3, 1993 [CH] Switzerland .............................. 1882/92

[51] Int. Cl.$^6$ ......................................................... A61K 9/62
[52] U.S. Cl. ...................... 424/461; 424/401; 424/436; 424/451; 424/459; 424/463; 424/474; 424/489; 549/546; 560/201; 560/220; 560/225
[58] Field of Search ...................................... 424/401, 451, 424/459, 461, 474, 489, 436; 560/201, 220, 225; 549/546

[56]    References Cited

U.S. PATENT DOCUMENTS 3,480,663  11/1969  Thiele ........................................ 260/482
4,256,600  3/1981  Lewis et al. .............................. 252/132

FOREIGN PATENT DOCUMENTS 0681891  6/1993  Switzerland .

OTHER PUBLICATIONS

CA 117: 55950(1992).
CA 113: 103206 (1990).
CA 89: 147103 (1978).
CA 108: 26959 (1988).
CA 84: 165073 (1973).
CA 78: 67001 (1973).
CA 71: 24728 (1969).
CA 67: 120173 (1967); CA 66: 28371 (1967).
Guenther Weitzel, *Chemical Abstracts*, 71(6): 24728k.
Masahiro Morioka et al., *Chemical Abstracts*, 84(23): 165073y.
Kyoichi Suga et al., *Chemical Abstracts*, vol. 85, 1976, 177635s.
Kikumasa Sato et al., *Chemical Abstracts*, vol. 87, 1977, 23559z.
Misao Yagi et al., *Chemical Abstracts*, 89(17): 147103g.
J. A. Schofield et al., *Chemical Abstracts*, vol. 89, 1978, 5506s.
A. A. Kuliev et al., *Chemical Abstracts*, vol. 96, 1982, 159357a.
Eiichi Kitazawa et al., *Chemical Abstracts*, vol. 99, 1983, 35934d.
Yuzo Shioi et al., *Chemical Abstracts*, vol. 100, 1984, 100139d.
S. Teng et al., *Chemical Abstracts*, vol. 100, 1984, 210170q.
G. W. Dawson et al., *Chemical Abstracts*, 108(19): 163232q.
Toshiyuki Nishio et al., *Chemical Abstracts*, vol. 110, 1989, 152829e.
Marina Gallarate et al., *Chemical Abstracts*, vol. 110, 1989, 82382c.
Stig E. Friberg, "Microemulsions", J. Dispersion Science and Technology, 6 (3), 1985, pp. 317–337.
Leon M. Prince, *Microemulsions. Theory and Practice*, Academic Press, Inc., New York, 1977.
Kozo Shinoda et al., *Emulsions and Solubilization*, John Wiley & Sons, New York, 1968, pp. 1–9.
Michele Trotta et al., "Diffusion of Steriod Hormones from O/W Microemulsions: Influence of the Cosurfactant", Acta Pharm. Technol. 36(4), 1990, pp. 226–231.
J. H. Schulman et al., "Molecular Interactions at Oil/Water Interfaces", Trans Faraday Soc. 1940, 36, pp. 651–668.
H. F. Eicke, "The Microemulsion Concept in Nonpolar Surfactant Solutions", *Microemulsions*, Proc.Conf.Phys.Chem.Microemulsions, Plenum 1982, ed. I. D. Robb, pp. 17–32.
Ingvar Danielsson et al., "The Definition of Mircoemulsion", Colloids and Surfaces, 3 (1981), pp. 391–392.
Bo Gestblom et al., "Solubilization of Drugs in Microemulsions as Studied by Dielectric Spectroscopy", J. of Colloid and Interface Science, 155 (1993), pp. 392–401.
*The Merck Index*, 11th Edition, Merck & Co., Inc., Rahway, NJ, USA, p. 204 [1338.Borneol, 1339.Bornyl Acetate, 1342.d–Bornyl Isovalerate, 1343.Bornyl Salicylate]; p. 364 [2332.β–Citronellol]; p. 618 [3885.Farnesol]; p. 689 [4298.Geraniol]; p. 818 [5084.Isophytol]; p. 916 [5723.Menthol]; p. 1173 [7362.Phytol]; p. 1481 [9333.Thymol].

*Primary Examiner*—Jyothsna Venkat
*Attorney, Agent, or Firm*—Foley & Lardner

[57]    ABSTRACT

New biotenside esters, processes for their preparation and their use as solvents and hydrotropic agents (coemulgators) in the preparation of spontaneously dispersible concentrates containing therapeutic or cosmetic agents are described.

16 Claims, No Drawings

BIOTENSIDE SOLVENTS FOR PHARMACEUTICALS AND COSMETICS

INTRODUCTION

The present invention relates to new biotenside esters, to processes for their production and to their use as solvents and hydrotropic agents or coemulgators in the preparation of spontaneously dispersible concentrates containing therapeutic or cosmetic active substances.

In the Swiss Patents No.678276-0, 681153-0, 681152-8 and 681'891-2 spontaneously dispersible concentrates are described which contain as active components compounds, which are water-insoluble, have an antitumor activity and consist of sterols, their glucosides and posphatides as well as the esters of these compounds with fatty acids, retinoic acids and with azafrin acid.

The spontaneously dispersible concentrates contain as the hydrotropic agent and coemulgator esters of an aliphatic alcohol with an aliphatic carbonic acid, such as e.g. isopropyllaurate, hexyllaurate, decyllaurate, isopropylmyristate, isopropylpalmitate and/or laurylmyristate.

It was found that the newly synthetized biotenside esters lend themselves much better for the preparation of spontaneously dispersible concentrates containing pharmaceutical and/or cosmetic active substances than the solvents or coemulgators which are customarily used.

When the spontaneously dispersible concentrates containing the new inventive biotenside esters are diluted with water, they produce thermostable microemulsions with globular micelles of a very small size. The hydrodynamic radius of the automatically emerging micelles is well below the dimension which was up-to-now achievable. The "ultra-microemulsions" have an excellent phase-stability.

As a consequence, the intensified capacity of such microemulsions for permeation and spreading increases the bioavailability of the pharmaceutical and/or cosmetic active substances contained in these inventive concentrates and potentially enhances their dose effectiveness and/or reduces their relative toxicity.

DESCRIPTION OF THE INVENTION

The new biotenside esters have the general formulae (I) to (VII):

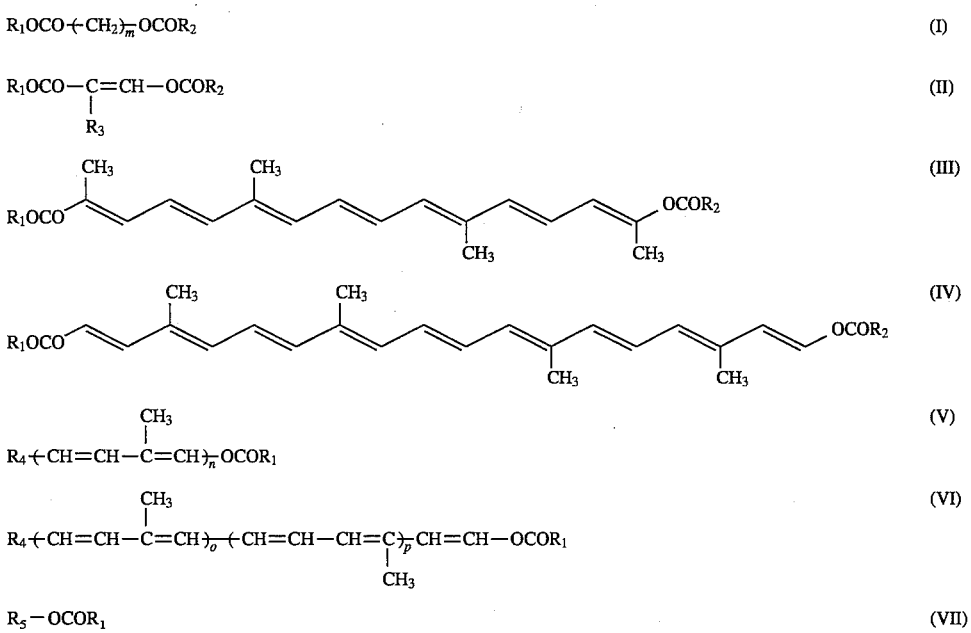

whereby in the formulae (I) to (VII)

$R_1$ stands for
- 3,7-Dimethyl-6-octenyl, (β-Rhodinyl) [CITRONELLYL]
- (E)-3,7-Dimethyl-2,6-octadien-1-yl [GERANYL]
- 3,7,11-Trimethyl-2,6,10-dodecatrien-1-yl [FARNESYL]
- 3,7,11,15-Tetramethyl-2-hexadecen-1-yl [PHYTYL] or
- 3,7,11,15-Tetramethyl-1-hexadecen-3-yl [ISOPHYTYL]

$R_2$ means
hydrogen, halogen, $C_1$ to $C_4$ alkyl, 3,7-Dimethyl-6-octenyl, (E)-3,7-Dimethyl-2,6-octadien-1-yl; 3,7,11-Trimethyl-2,6,10-dodecatrien-1-yl; 3,7,11,15-Tetramethyl-2-hexadecen-1-yl or 3,7,11,15-Tetramethyl-1-hexadecen-3-yl m designates the numbers 1 to 18

$R_3$ stands for hydrogen or methyl $R_5$ symbolizes a $C_1$ to $C_{32}$ alkyl or $C_2$ to $C_{32}$ alkenyl or alkapolyen group n, o, p mean the numbers 1, 2, 3, 4 or 5 and $R_4$ stands for one of the radicals of the following formulae:

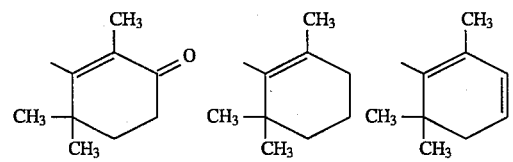

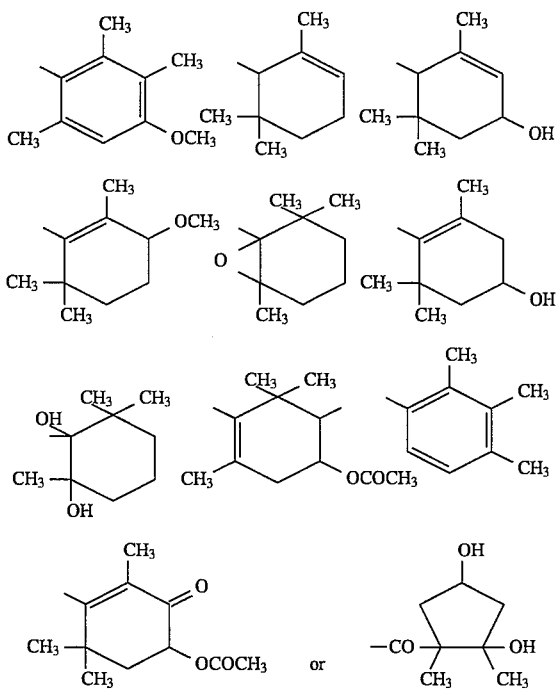

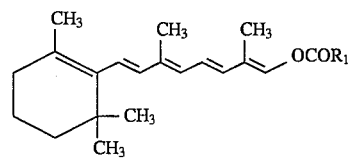

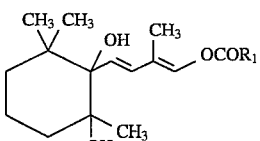

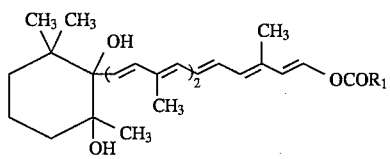

In accordance with the starting compounds maleic acid and fumaric acid, the compounds of formulae (II) can take on a cis- or trans-form. The term halogen at $R_2$ stands for fluorine, chlorine, bromine or iodine, and particularly chlorine. The term $C_1$ to $C_4$ alkyl comprises methyl, ethyl, propyl, isopropyl, n-butyl, sec.-butyl or tert.-butyl, specifically methyl and ethyl respectively. The alkyl, alkenyl or alkapolyen groups at $R_5$ can be straight chained or branched and preferably have chains made up with 8 to carbon atoms. The term alkapolyen comprises the corresponding alkadienes, alkatrienes, alkatetraenes, alkapentaenes, alkahexaenes and alkaheptaenes. Examples of such groups at $R_5$ are, inter alia:

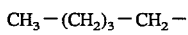
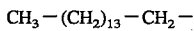
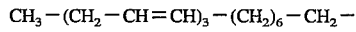
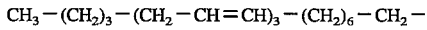
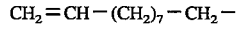
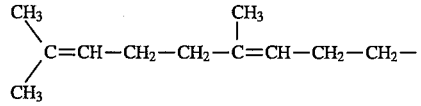
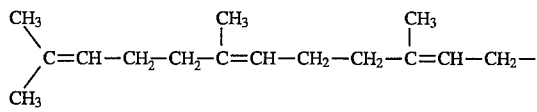

The most important compounds according to formulae (V) and (VI) are characterized by formulae (VIII), (IX) and (X):

in which $R_1$ means 3,7-Dimethyl-6-octenyl; (E)-3,7-Dimethyl-2,6-octadien-1-yl; 3,7,11-Trimethyl-2,6,10-dodecatrien-1-yl; 3,7,11,15-Tetramethyl-2-hexadecen-1-yl, or 3,7,11,15-Tetramethyl-1-hexadecen-3-yl The radicals 3,7-Dimethyl-6-octenyl; (E)-3,7-Dimethyl-2,6-octadien-1-yl; 3,7,11-Trimethyl-2,6,10-dodecatrien-1-yl; 3,7,11,15-Tetramethyl-2-hexa-decen-1-yl. or 3,7,11,15-Tetramethyl-1-hexadecen-3-yl, as well as the radicals according to formulae:

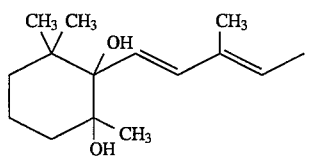

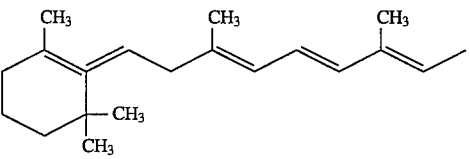

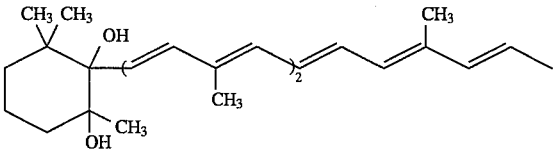

can be present in different stereoisomeric or rotational forms.

Of particular importance are the biotenside esters according to the general formulae (I), (II), (VII), (VIII), (IX) and (X):

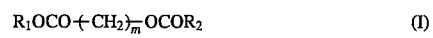  (I)

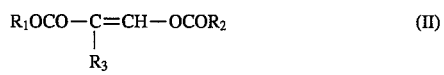  (II)

  (VII)

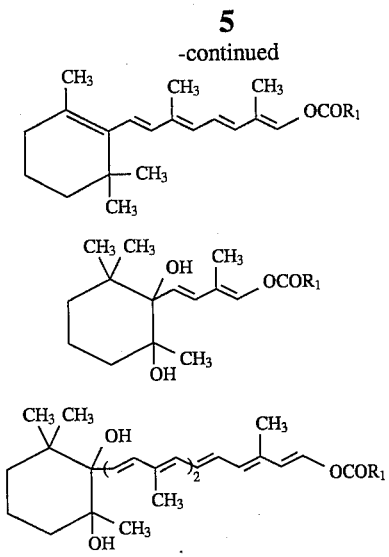

in which $R_1$ represents citronellyl, geranyl, farnesyl, phytyl or isophytyl; $R_2$ stands for hydrogen, chlorine, methyl, ethyl, citronellyl, geranyl, farnesyl, phytyl or isophytyl; $R_3$ means hydrogen and $R_5$ symbolizes a $C_8$ to $C_{22}$ alkyl or a $C_8$ to $C_{22}$ alkenyl and alkapolyen group respectively.

Examples of inventive new biotenside esters are, inter alia:

Succinic acid bis-phytyl ester
Malonic acid bis-phytyl ester
Glutaric acid bis-phytyl ester
Fumaric acid bis-phytyl ester
Adipic acid bis-phytyl ester
Pimelic acid bis-phytyl ester
Suberic acid bis-phytyl ester
Azelaic acid bis-phytyl ester
Sebacic acid bis-phytyl ester
Glutaric acid bis-citronellyl ester
Fumaric acid bis-citronellyl ester
Azelaic acid bis-citronellyl ester
Sebacic acid bis-citronellyl ester
All trans retinoic acid citronellyl ester
All trans retinoic acid geranyl ester
All trans retinoic acid farnesyl ester
All trans retinoic acid phytyl ester
Azafrin acid phytyl ester
Crotonyl-phytolate
Valeryl-phytolate
Pivaloyl-phytolate
Caproyl-phytolate
Pelargonyl-phytolate
10-Undecenoyl-phytolate
trans-2-Dodecenyl-phytoloate
Lauryl-phytolate
Palmitoyl-phytolate
Elaic acid-phytolate
Linoleic acid-phytolate
Linolenic acid-phytolate
Succinic acid methyl-phytyl-diester
Succinic acid ethyl-phytyl-diester
Glutaric acid ethyl-phytyl-diester
Glutaric acid methyl-phytyl-diester
Azelaic acid methyl-phytyl-diester
Sebacic acid methyl-phytyl-diester The new biotenside esters according to formulae (I) to (X) may generally be prepared by the following processes, which are known per se:

a) Reaction of a compound of formulae (XI) and (XII):

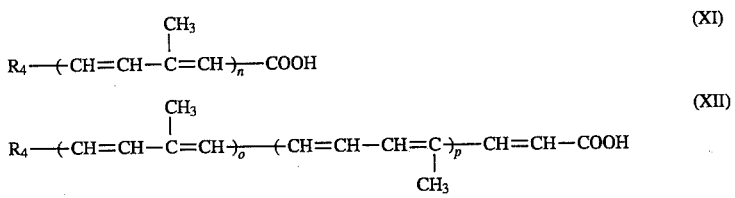

in which the letters n, o und p designate the numbers 1, 2, 3, 4 or 5 and $R_4$ stands for one of the radicals according to the following formulae:

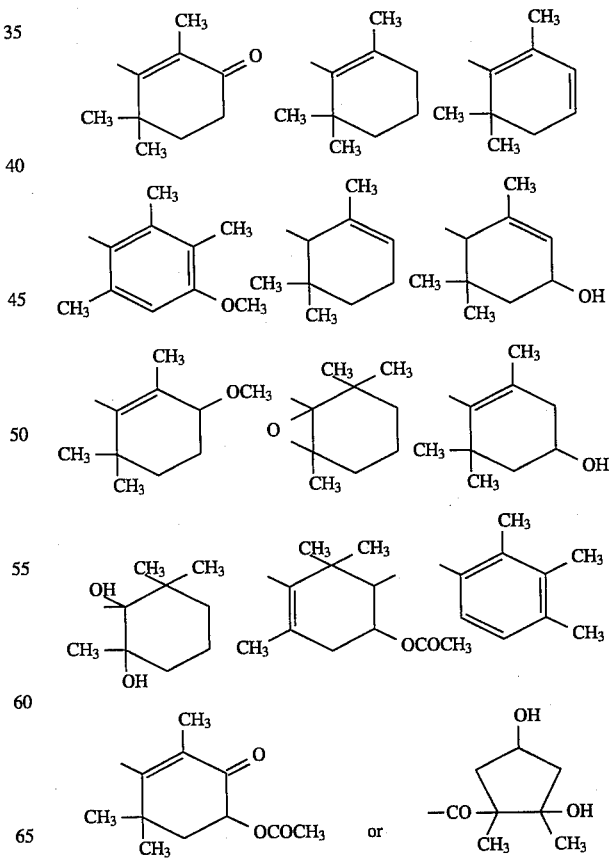

with N,N'-carbonyldiimidazole at a temperature of 25° to 70° C. under addition of a catalytic amount of an alcoholate in an indifferent solvent, such as, e.g., tetrahydrofuran, benzene or chloroform, followed by alcoholysis of the imidazolides formed with citronellol, geraniol, farnesol, phytol or isophytol.

b) Formation of the chloride or the bromide of a compound of the formulae (XI), (XII), (XIII), (XIV), (XV), (XVI) and (XVII)

$$R_4-(-CH=CH-\underset{CH_3}{C}=CH-)_n-COOH \quad (XI)$$

$$R_4-(-CH=CH-\underset{CH_3}{C}=CH-)_o-(-CH=CH-CH=\underset{CH_3}{C}-)_p-CH=CH-COOH \quad (XII)$$

in which the letter n means the numbers 1, 2, 3, 4 or 5 and $R_4$ stands for one of the radicals of formulae:

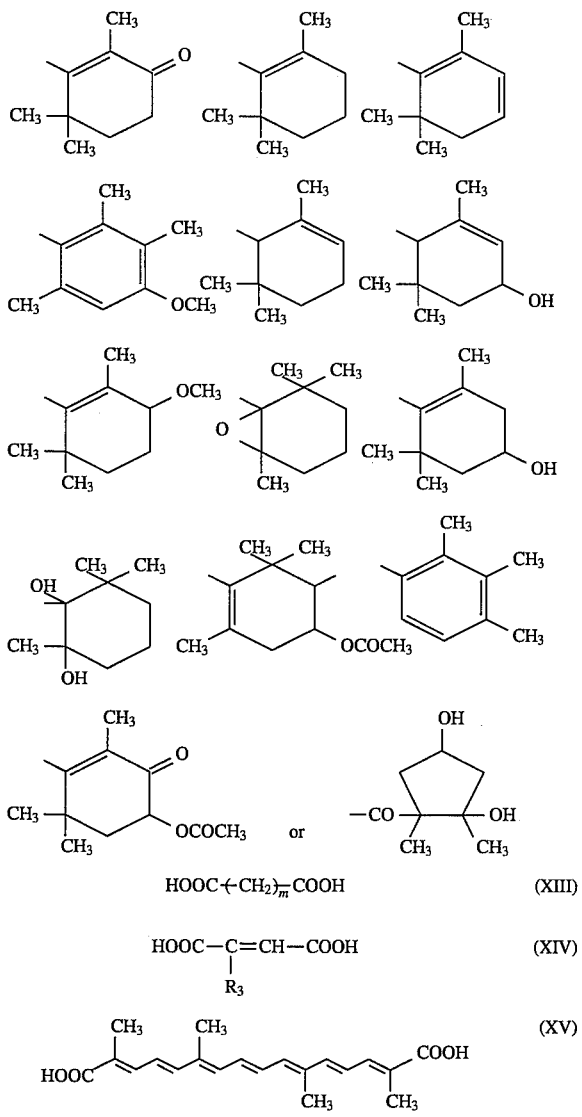

$$HOOC-(-CH_2-)_m-COOH \quad (XIII)$$

$$HOOC-\underset{R_3}{C}=CH-COOH \quad (XIV)$$

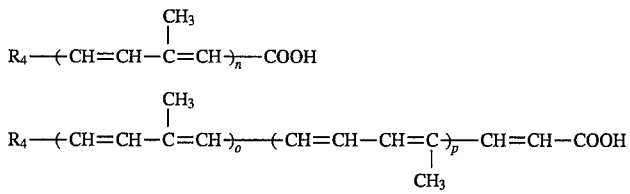

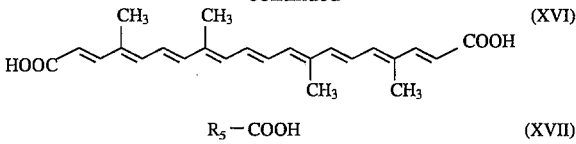

$$R_5-COOH \quad (XVII)$$

whereby in formula (XIII) the letter m means the numbers 1, 2, 3, 4 or 5, $R_3$ in formula (XIV) stands for hydrogen or methyl and $R_5$ in formula (XVII) designates a $C_1$ to $C_{32}$ alkyl or a $C_2$ to $C_{32}$ alkenyl or alkapolyen group, with a chlorination or bromination agent, such as e.g. thionylchloride, oxalylchloride or oxalylbromide and subsequent reaction with citronellol, geraniol, farnesol, phytol or isophytol at a temperature of 40° to 120° C. in an indifferent solvent, such as toluene or xylene and in the presence of a catalyst, such as dimethylformamide or p-dimethylaminopyridin.

The new biotenside esters according to formulae (I) to (VII) can be used as Solvents or Cotensides (i.e Hydrotropes) in the preparation of spontaneously dispersible concentrates, which contain pharmaceutically and/or cosmetically active compounds. For this reason, spontaneously dispersible concentrates of pharmaceutical and cosmetic substances which contain as solvents or coemulgators (hydrotropes) the novel biotenside esters according to formulae (I) to (VII) are also a subject matter of the present invention. When treated with water, such concentrates render microemulsions having micelles with a hydrodynamic radius the size of which is far smaller than was customary up to now.

Thanks to the small particle size of the micromicelles generated, the "ultramicroemulsions" possess not only excellent phase stability, but also much improved membrane permeability and spreading properties. This leads to the consequence that their biological action pattern is improved: the better bioavailability of the active substances contained in the microemulsions also expresses itself remarkably in enhanced dose-efficacy and leads to reduced relative toxicity.

All experimental observations gained with such ultramicroemulsions can be explained consistently and uniformly on the basis of the assumption that the selected surfactants and cotensides, taken as a balanced system, form organized aggregates, so-called Micelles, in the aqueous phase. These have a more or less globular shape and a hydrodynamic radius of 1,5 to 3 nm. The tensides and hydrotropes (cotensides) produce a boundary layer between the outer, aqueous phase and the inner, oily phase of the microemulsion [containing the pharmaceutical or cosmetic active substances, dissolved in the biotenside coemulgator according to formulae (I) to (VII)], a process which prevents the mixing of the two phases. In the oily, inner phase the active substance molecules are present in monomeric or in oligomerically agglomerated form.

The micelles of the inventive ultramicroemulsions, containing in their inner phase the active substances, are protected at the interface by a tenside coating or umbrella, which enables them to penetrate the cell membrane and diffuse into the cell plasma. Diffusion across the plasma membrane of tumour cells occurs exclusively on the strength of molecular movements. The direction which is taken by any concrete diffusion process, is determined by the differential in concentration existing at the plasma membrane between the outside and the inside compartments of the individual cell. Diffusion continues until the gradient has been reduced. The concentration of active substance or of an active substance system (a "multiple drug system") is equalized between the outside and the inside of the cell. This may include "slow release effects". Self-diffusion processes of this kind occur independently of any energy input. They are not related to the ordinary metabolic processes of the cell.

The speed of diffusion is governed by Fick's Law of diffusion, in direction of a concentration gradient $$\frac{dm}{dt}\frac{1}{q} = -D\frac{dc}{dx} \qquad \text{EQUATION (A)}$$

where dm signifies the amount in Mol of active substance molecules which penetrate a cell surface q (in cm$^2$) per time-unit dt (in seconds). D is the coefficient of diffusion and dc the concentration differential over the distance dx.

According to Nernst the diffusion coefficient is dependent on the absolute temperature T and the friction resistance f $$D = \frac{R}{N}\frac{T}{f} = \frac{kT}{f} \qquad \text{EQUATION (B)}$$

Friction resistance f is, according to Stoke's Law, $$f = 6\pi\eta r \qquad \text{EQUATION (C)}$$

a function of the viscosity of the diffusing solution and of the radius of the diffusing particles. By substituting f with $f = 6\pi\eta r$ in the Nernst equation, one obtains the SUTHERLAND-EINSTEIN equation for the DIFFUSION COEFFICIENT $$D = \frac{RT}{N}\frac{1}{6\pi\eta r} = \frac{kT}{6\pi\eta r} \qquad \text{EQUATION (D)}$$

where k stands for the Boltzmann constant.

If for a particular diffusion process, one assumes a regular reduction of concentration in the membrane of the tumour cell, then the expression $\frac{dc}{dx}$ in the diffusion law can be restarted as $\frac{\Delta c}{x}$ (=concentration differential $\Delta c$ over a cell membrane of thickness x). x is a constant value for a specific (homogenous) membrane. For this reason, it can be combined with the diffusion coefficient to express a new constant, the permeability coefficient P, $$P = \frac{D}{x} \qquad \text{EQUATION (E)}$$

The expression dm/dt 1/q in the diffusion equation is called FLUX J. It has the dimension Mol per second per cm$^2$. The negative sign on the right side of the equation indicates that the transport of the molecules of the active substance or the system's preparation containing the active substances flows in the direction of the decreasing concentration.

Therefore, we have $$\text{EQUATION (F)}$$
$$J = -F\Delta c = -\frac{RT}{Nx}\frac{1}{6\pi\eta r}\Delta c = \frac{kT}{x}\frac{1}{6\pi\eta r} - \Delta c$$

It can be deduced from this equation that the velocity of the diffusion process across the cell membrane is governed by:

1. the concentration difference AC in the two compartments outside and inside the cell
2. the radius of the particles of the diffusing active substance or system's preparation
3. the viscosity of the diffusing aqueous solution (emulsion)
4. the temperature.

The proper solubilization of active substances, which are insoluble in water, by means of surfactants (tensides plus coemulgators) is a conditio sine qua non for achieving self-diffusion and hence transport of the active substances across biological cell membranes.

The inventive spontaneously dispersible concentrates contain:

0,001 to 30% by weight of one or more pharmaceutical (therapeutic) or cosmetic active substances 0,001 to 50% by weight of an ester of formulae (I) to (VII) according to the invention, and combinations of such esters respectively, used as solvents or hydrotropic agents.

0,001 to 90% by weight of a pharmaceutically acceptable surfactant or surfactant mixture, and optionally up to 10% by weight of a vitamin or provitamin 10% by weight of an antitumor agent of oily consistence up to 10% by weight of a free fatty acid or an amino acid, and if appropriate, customary excipients and/or diluents.

By the term pharmaceutical active substances are designated in the present case all active compounds which are currently being used therapeutically in human medicine. The list comprises e.g.:

Beta-Blockers

Pindolol [1-(4-Indolyloxy)-3-isopropylamino-2-propanol]

Propanolol [1-Isopropylamino-3-(1-naphthyloxy)-2-propanol]

Oxprenolol [1-(o-Allyloxyphenoxy)-3-isopropylamino-2-propanol]

Metoprolol [Di-{(+−)-1-(isopropylamino)-3-[p-(2-methoxyethyl)-phenoxy-2-propanol]-L (+) tartrate}]

Labetalol [5-[1-Hydroxy-2{(1-methyl-3-phenylpropyl-aminoethyl}salicylamide]

Diuretica

Acetazolamide [5-Acetamido-1,3,4-thiadiazol-2-sulfonamide]

Hydrochlorothiazide [6-Chlor-3,4-dihydro-2H-1,2,4-benzothiadiazin-7-sulfonamide-1,1-dioxide]

Chlortalidon [1-Oxo-3-(3-sulfamyl-4-chlorphenyl)-3-hydroxy-isoindolin]

Metolazon [7-Chlor-1,2,3,4-tetrahydro-2-methyl-4-oxo-3-o-tolyl-6-chinazolinsulfonamide]

Mild Sedatives

Diazepam [7-Chlor-1,3-dihydro-1-methyl-5-phenyl-2H-1,4-benzodiazepin-2-on]

Medazepam [7-Chlor-2,3-dihydro-1-methyl-5-phenyl-2H-1,4-benzodiazepin-2-on]

Strong Tranquillizers

Sulpirid [N-(1-Ethyl-2-pyrrolidinyl-methyl)-2-methoxy-5-sulfamoylbenzamide]

Muscle Relaxants

Baclofen [I]-(Aminoaethyl)-p-chlorhydrozimtsäure]

Antibiotics

Sulfamethoxazol [5-Methyl-3-sulfanilamido-isoxazole]

Trimethoprim [2,4-Diamino-5-(3,4,5-trimethoxybenzyl)-pyrimidin]

Chloramphenicol [D (−)-threo-2-dichlor-acetamido-1-(4-nitrophenyl)-1,3-propandiol]

Cefaclor [3-Chloro-7-D(2-phenyl-glycinamido)-cephalosporan acid monohydrate]

Cefradin [7-{D-2-Amino-2-(1,4-cyclohexadien-1-yl)-acetamido}-3-methyl-cephalosporan acid]

Bacampicillin [1-Ethoxycarbonyloxy-ethyl-6-(D-α-aminophenyl-acetate-amido)-penicillinate]

Minocyclin [7-Diethylamino-6-desoxy-6-desmethyltetracyclin]

Sulfadoxin [N'-(5,6-Dimethoxy-4-pyrimidinyl)-sulfanilamide]

Sulfamethoxazol [3-Methyl-3-sulfanil-amido-isoxazole]

Sulfisoxazol [3,4-Dimethyl-5-sulfanil-amido-isoxazole]

Sulfadimethoxin [2,4-Dimethoxy-6-sulfanilamido-1,3,diazin]

Dermatologica

Chlorquinaldol [5,7-Dichlor-8-hydroxy-chinaldine]

Crotamiton [N-Crotonyl-N-ethyl-o-toluidene]

Diamthazol [6(−)2-Dimethylamino-ethoxy-(β-diaethylamino-)-benzothiazol-dihydrochloride]

Flumethason-pivalat [6α,9-Difluor-11β,17,21-trihydroxy-16α-methyl-pregna-1,4-dien-3,20,dion-21-pivalate]

Tretinoin [Vitamin-A-acid]

Corticosteroids

Cortison [17α-21,Dihydroxy-pregn-4-en-3,11,20-trien-21-acetate]

Prednison [11β-17,21-Trihydroxy-pregna-1,4-dien-3,20-dion]

Dexamethason [9-Fluor-11β,17,21-dihydroxy-16α-methyl-pregna-1,4-dien-3,20-dion]

Desoxycorton-acetat [21-Hydroxy-pregn-4-en-3,20-dion-acetate]

Coronary Agents

Pentaerythrityltetranitrate (PETN)

Nitroglycerin (Glyceryltrinitrate)

Pindolol [1-(4-Indolyloxy-3-isopropylamino-2-propanol]

Cytostatica

Melphalan [p-Di-(2-chloräthyl)-amino-L-phenylalanin]

Procarbazin [p-(N'-Methyl-hydrazinomethyl)-N-isopropyl-benzamide]

Dactinomycin [Actinomycin D]

Polyestradiolphosphate

Cyclophosphamide [N,N-bis-(β-Chlorethyl)-amino-1-oxa-3-aza-2-phosphocyclohexan-2-oxide]

Antiinflammatory Agents

Mefenamin acid [3-Xylyl-2-aminobenzoe acid]

Dexamethason [9-Fluor-11β,17,21-trihydroxy-16α-methyl-pregna-1,4-dien-3,20-dion]

Hydrocortisone [17α-Hydroycorticosterone]

Coronary Dilators

Nifedipin [1,4-Dihydro-2,6-dimethyl-4-(o-nitrophenyl)-pyridin-3,5-dicarbonic acid-dimethylester]

Isosorbid-dinitrate [1,4;3,6-Dianhydrosorbit-2,5-dinitrate]

Nitroglycerine (Glyceryl-trinitrate)

Dipyramidol [2,6-Bis-(diethanolamino)-4,8-dipiperidino (5,4-dipyrimidin)]

Peripheric Vasodilators

Cinepazid [4-(-3,4,5-Trimethoxy-cinnamoyl)-1-piperazin-acetic acid-pyrrolidide]

Cyclandelate [3,3,5-Trimethyl-cyclohexylmandelate]

Cinnazarin [1-trans-Cinnamyl-4-diphenylmethyl-piperazin]

Pentoxyfyllin [3,7-Dimethyl-1-(5-oxo-hexyl)-xanthin]

Antirythmica

Procainamide [4-Aminobenzoe acid-β-diethylaminoethylamide]

Disopyramid [4-Diisopropylamino-2-phenyl-2-(2-pyridyl)-butyramide]

Anti Gout Agents

Allopurinol [1H-Pyrazolo-(3,4-d)-pyrimidin-4-ol]

Antiepileptica

Phenytoin {Diphenylhydantoin}; [5,5-Diphenyl-2,4-imidazolidin-dion]

Carbamazepin [5-Carbamoyl-5H-dibenz(b,f)azepin]

Antihistaminica

Chlorphenamine [{3-(p-Chlorphenyl)-3-(2-pyridyl)-propyldimethylamine}]

Clemastin {Hydrogenfumarate}; [1-Methyl-2-{2-(α-methyl-p-chlor-diphenylmethoxy) ethyl}pyrrolidin]

Mequitazin [10-(3-Chinuclidinylmethyl) phenothiazin]

Alimemazin [10-(3-Dimethylamino-2-methyl-propyl)-phenothiazin]

Agents Against Indisposition and Dizziness

Domperidon [5-Chlor-1-{1-(3-[2-oxo-1-benzimidazolinyl]-propyl)-4-piperidyl}2-benzimidazolinone]

Betahistin [2-{2-Methylaminoethyl} pyridin]

Metoclopramide [4- Amino-5-chlor-N-(2-diethylamino äthyl)-2-methoxybenzamide]

Blood Pressure Reducing Agents

Reserpin [3,4,5-Trimethoxybenzoyl-methylreserpate]

Rescinnamin [3,4,5-Trimethoxy-methylreserpate]

Methyldopa {L-α-Methyldopa}; [L-3-(3,4-Dihydroxyphenyl)-2-methylalanin]

Clomidinhydrochlorid [2,6-Dichlor-N-2-imidazoidinyliden-benzamin hydrochloride]

Sympathomimetica

Isoproterenol [N-Isopropyl-nor-adrenaline]

Etilefrine [DL-1-{α-Ethylaminomethyl}-m-hydroxybenzylalcohol]

Expectorantia

Carbocystein [(S-Carboxymethyl) cystein]

Bromhexin [N-Cyclohexyl-N-methyl-(2-amino-3,5-dibrom-benzyl) amin HCL]

L-Ethylcystein

L-Methylcystein

Oral Antidiabetica

Glibenclamide [N-4-2-(5-Chlor-2-methoxy-benzamido)-ethylphenylsulfonyl-N'-cyclohexyl-urea]

Tolbutamide [N-(4-Tolylsulfonyl)-N'-n-butyl-urea]

Cardiovascular Agents

Ubidecarenon

Adenosin [6-Amino-9-β-D-ribo-furanosyl-9H-purin]

Immunosuppressivum

Ciclosporin

The new biotenside esters according to formulae (I) to (VII) are particularly useful solvents and cotensides (hydrotropes) when employed in the preparation of spontaneously dispersible concentrates containing the following antitumor compounds:

Ergosta-5,7-dien-3-ol-9-hexadecenoate
(Ergosta-5,7-dienylpalmitoelate)
Ergosta-8,22-dien-3-0114-methyl-4,9-octadecenoate
(14α-Methylergosta-8,22-dienyloleate)
Lanost-8-en-3-ol-9-octadecenoate
(Dihydrolanosterol-oleate)
Ergost-5-en-3-ol-9,12,15-octadecatrienoate
(Dihydrobrassicasteryl-linolenate)
Ergost-5-en-3-ol-9,12-octadecadienoate
Ergost-5-en-3-ol-9-octadecenoate
(Dihydrobrassicasteryl-olaete)
Ergosta-7,24 (28)-dien-3-ol-4-methyl-9-octadecenoate
(Gramisteryl-oleate)
Stigmasta-8,24 (28)-dien-3-ol-9,12-octadecadienoate
($\Delta^7$-Avenasteryl-linoleate)
Ergosta-7,24 (28)-dien-3-ol-4-methyl-9,12-octadecadienoate
(Gramisteryl-linoleate)
Stigmast-24 (28)-en3-ol-9,12-octadecadienoate
Ergosta-5,22-dien-3-ol-4,23-dimethyl-9-octadecenoate
Ergostan-3-ol-4-methyl-9-octadecenoate
5α-Stigmastan-3-β-ol-linolenate
5α-Stigmastan-3-β-ol-oleate
Stigmastan-3-ol-9,12-octadecadienoate
(5α-Stigmastan-3-β-ol-linoleate)
22-Dihydrospinasteryl-linoleate
Ergosta-5,7,22-trien-3-ol-9,12-octa-decadienoate
(Ergosterol-Linoleate)
Stigmasta-5,24 (28)-dien-3-ol-9-octadecenoate
Stigmasta-5,24 (28)-3-ol-9,12-octadecadienoate
Stigmasta-5-en-3-ol-5,8,11,14-eicosatetraenoate
(β-Sitosterol-Arachidonate)
Ergost-5-en-3-ol-5,8,11,14-eicosatetraenoate
Stigmasta-7,24(28)-dien-ol-4-methyl-9,12-octadecadienoate
Cholest-5-en-3-ol-(3β)-9-hexadecenoate
(Cholesteryl-trans-9-hexadecenoate)
Ergost-7-en-3-ol-9,12,15-octadecatrienoate
Ergost-5-en-3-ol-9,12,15-octadecatrienoate
(Campesteryl-linolenate)
Ergostan-3-ol-9,12-octactadecadienoate
Cholest-7-en-3-ol-9,12-octaoctadecadienoate
Ergosta-5,24-(28)-dien-3-ol-9-hexadecenoate
Cholestan-3-ol-9-hexadecenoate
Ergosta-5,22-dien-3-ol-octadecenoate
(Brassicasteryl-oleate)
Cholest-7-en-3-ol-9-octadecenoate
(Lathosteryl-oleate)
Lanosta-8,24-dien-3-ol-9-octadecenoate
(Lanosterol-oleate)
Stigmasta-5,24(28)-dien-3-ol-9octadecenoate
(Fucosteryl-oleate)
Cholesta-5,22-dien-3-ol-9.octadecenoate
(Desmosteryl-oleate)
Ergost-5-en-3-ol-12-octadecadienoate
(Campesteryl-linoelate)
Ergosta-5,22-dien-3-ol-9-octadecenoate
Ergost-22-en-3-ol-9-hexadecenoate
Cholesta-5,22-dien-3-ol-9-hexadecenoate
Ergosta-5,22-dien-3-ol-9,12-octadecadienoate
(Brassicasteryl-linoleate)
Ergosta-7,24 (2β)-dien-3-ol-9,12-octadecadienoate
Stigmasta-5,22-dien-3-ol-9,12,15-octadecatrienoate
(Stigmasteryl-linolenate)
Stigmasta-5,22-dien-3-ol-9,12-octadecadienoate (Stigmasteryl-linoleate)
Cholest-5-en-3-ol-(3β)-5,8,11,14-eicosatetraenoate
Cholest-5-en-3-ol-(3β)-4,7,10,13,16,19-docosahexaenoate
Cholest-5-en-3-ol-(3β)-9,12-octadecadienoate
Cholesta-8, (14), 24, dien-3-ol-9-octadecenoate
(Zymosteryl-oleate)
Ergost-5-en-3-ol-9-octadecenoate
(Campesteryl-oleate)
Cholest-5,7,9 (11)-trien-3-ol-9-octadecenoate
(Cholesta-5,7,9 (11))-trien-3β-yl-oleate)
Ergosta-5,7,22-trien-3-ol-9-hexadecenoate
(Ergosteryl-9-hexadecenoate)
Cholest-5-en-3-ol-(3β)-11-octadecenoate
(Cholesteryl-11-octadecenoate)
Cholest-5-en-3-ol-(3β)-9,12-octadecadienoate
(Cholesteryl-9,12-octadecadienoate)
Cholest-5-en-3-ol-(3β)-9-octadecenoate
(Cholesterol-elaidate)
5a-Stigmasta-7,22-dien-3β-ol-oleate
(α-Spinasterol-oleate)
Cholest-5-en-3-ol-(3β)-9-hexadecenoate
(Cholesterol-palmitoleate)
Cholestan-3-ol-9,12,15-octadecatrienoate
(Cholestanol-linolenate)
Cholest-5-en-3-ol-(3β)-11-octadecenoate
(Cholesterol-11-octadecenoate)
Cholesta-5,7-dien-3-ol-9-octadecenoate
Cholesta-5,7-dien-(3β)-ol-linoleate
(Cholecalciferon-linoleat; Cholecalciol-linoleate)
Ergosta-5,7,22-trien-3-ol-9-octadecenoate
(Ergosterol-oleate)
Stigmast-5-en-3-ol-9-octadecenoate
(β-Sistosterol-oleate)
Stigmast-5-en-3-ol-9,12-octadecadienoate
(β-Sistosterol-linoleate)
Stigmast-5-en-3-ol-9,12,15-octadecatrienoate
(β-Sistosterol-linolenate)
Cholest-5-en-3-ol-(3β)-9,12,15-octadecatrienoate
(Cholesteryl-linolenate)
Cholestan-3-ol-9-octadecenoate
(Cholestanol-oleate)
Cholestan-3-ol-9,12-octadecadienoate
(Cholestanol-linoleate)

Cholest-5-en-3-ol-(3β)-9-hexadecenoate
(Cholesterol-9-hexadecenoate)
Cholest-5-en-3-ol-(3β)-5,8,11,14-eicosatetraenoate
(Cholesterol-arachidonate)
Cholest-5-en-3-ol-(3β)-9,12-octadecadienoate
(Cholesterol-linoleate)
Cholest-5-en-3-ol-(3β)-9-octadecenoate
(Cholesterol-oleate)
β-Sitosterol-undecenoate
β-Sitosterol-lauroylate
β-Sitosterol-palmitate
Stigmasterol-undecenoate
Stigmasterol-laurate
Stigmasterol-palmitate
γ-Sitostanol-oleate
γ-Sitostanol-linoleate
γ-Sitostanol-linolenate
γ-Sitosterol-oleate
Cholest-5-en-3α-ol-oleate
5-α-Stigmastan-3β-ol-oleate
5-α-Stigmastan-3β-ol-linolenate
Cholesta-5,7-dien-3β-ol-linoleate
Cholecalciferol-linolenat (Cholecalciol-linoleate)
10-α-Ergosta-5,7,22-trien-3β-ol-linoleate
Stigmast-5-en-3-ol-dodecenoate
(β-Sitosterol-2-dodecenoate)
Ergost-5-en-3-ol-dodecenoate
(Campesteryl-10-dodecenoate)
Cholest-7-en-3-ol-dodecenoate
Stigmasta-5,22-dien-3-ol-dodecenoate
(Stigmasterol-2-dodecenoate)
γ-Sitosterol-dodecenoate
Cholest-5-en-3-ol-10-undecenoate
Cholest-5-en-3-ol-2-dodecenoate
5-Cholestan-3β-ol-2-dodecenoate
Ergosta-5,7,22-trien-3-ol-all-trans-retinate
Ergosta-5,7,22-trien-3-ol-13-cis-retinate
Cholest-5-en-13-cis-retinate
Stigmast-5-en-3-ol-all-trans-retinate
(β-Sitosterol-all-trans-retinate)
Stigmast-5-en-3-ol-13-cis-retinate
(β-Sitosterol-13-cis-retinate)
Stigmast-5-en-3-ol-azafrinate
Stigmasta-5,22-dien-3-ol-all-trans-retinate
(Stigmasterol-all-trans-retinate)
Stigmasta-5,22-dien-3-ol-13-cis-retinate
(Stigmasterol-13-cis-retinate)
Stigmasta-5,22-dien-3-ol-arachidonate
Stigmasta-5,22-dien-3-ol-azafrinate
Stigmasta-5,22-dien-3-ol-1,2-dipalmitoyl-glycero-phosphatide
Stigmasta-5,22-dien-3-ol-1,2-dipalmitoyl-glycero-thiophosphatide
Ergosta-5,7,22-trien-3-ol-1,2-dipalmitoyl-glycero-phosphatide
Ergosta-5,7,22-trien-3-ol-crotonate
Ergosta-5,7,22-trien-3-ol-caproylate
Ergosta-5,7,22-trien-3-ol-10-undecenoate
Ergosta-5,7,22-trien-3-ol-2-trans-dodecenoate
Ergosta-5,7,22-trien-3-ol-palmitate
Ergosta-5,7,22-trien-3-ol-oleate
Ergosta-5,7,22-trien-3-ol-linoleate
Ergosta-5,7,22-trien-3-ol-linolenate
Ergosta-5,7,22-trien-3-ol-arachidonate
Ergosta-5,7,22-trien-3-ol-azafrinate
β-Estradiol-3,17-di-all trans-retinate
β-Estradiol-3-benzoate-17-retinate
Cholecalciferol-caproylate
Ergocalciferol-caproylate
Cholecalciferol-10-undecenoylate
Ergocalciferol-10-undecenoylate
Cholecalciferol-laurate
Ergocalciferol-laurate
Cholecalciferol-palmitate
Ergocalciferol-palmitate
Cholecalciferol-linoleate
Ergocalciferol-linoleate
Cholecalciferol-linolenate
Ergocalciferol-linolenate
Cholecalciferol-all trans-retinate
Ergocalciferol-all trans-retinate
Cholecalciferol-3-ol-1,2,-dipalmitoylglycero-phosphatide
Cholecalciferol-3-ol-1,2,-dipalmitoylglycero-thiophosphatide
Cholecalciferol-geranyl-phosphatide
Cholecalciferol-farnesyl-phosphatide
Ergocalciferol-3-ol-1,2,-dipalmitoyl-glycero-phosphatide
Ergocalciferol-3-ol-1,2,-dipalmitoyl-glycero-thiophosphatide
Ergocalciferol-geranyl-phosphatide
Ergocalciferol-farnesyl-phosphatide
DL-α-Tocopheryl-10-undecenoate
DL-α-Tocopheryl-palmitate
DL-α-Tocopheryl-all trans-retinate
DL-α-Tocopheryl-13 cis-retinate
Malonic acid bis-stigmasteryl ester
Succinic acid bis-stigmasteryl ester
Glutaric acid bis-stigmasteryl ester
Adipinic acid bis-stigmasteryl ester
Pimelic acid bis-stigmasteryl ester
Suberiic acid bis-stigmasteryl ester
Azelaic acid bis-stigmasteryl ester
Sebacic acid bis-stigmasteryl ester
Azelaic acid bis-β-sitosteryl ester
Sebacic aicd bis-β-sitosteryl ester
Azelaic acid bis-ergosteryl ester
Sebacic acid bis-ergosteryl ester
Azelaic aid bis-cholesteryl ester
Sebacic acid bis-cholesteryl ester
Maleic acid bis-stigmasteryl ester
Fumaric acid bis-stigmasteryl ester
Maleic acid bis-β-sitosteryl ester
Fumaric acid bis-β-sitosteryl ester Maleic acid bis-ergosteryl ester
Fumaric acid bis-ergosteryl ester
Maleic acid bis-cholesteryl ester
Fumaric acid bis-cholesteryl ester
Azelaic acid calciferyl diester
Sebacic acid calciferyl diester
Azelaic acid cholecalciferyl diester
Sebacic acid cholecalciferyl diester
Azelaic acid DL-α-tocopheryl diester
Sebacic acid DL-α-tocopheryl diester The surfactants or surfantant mixtures to be employed according to the invention can be anionic, cationic, amphoteric or non-ionic. Ideally, they are non-ionic and have an HLB-value (i.e. a hydrophilic-lipophilic balance) of between 2 and 18; preferably, it is between 2 and 6 on the one hand and 10 and 15 on the other hand. HLB values describe the hydrophilic and lipophilic properties of an emulsifier. In this context see "Hydrophile-Lipophile Balance: History and recent Developments" by Paul Becher in Journal of Dispersion Science and Technology, 5 (1), 81–96 (1984).

Suitable anionic surfactants can be both socalled water-soluble soaps and water-soluble synthetic compounds.

Suitable soaps are the alkali metal salts, alkaline earth metal salts or optionally substituted ammonium salts of higher fatty acids ($C_{12}$ to $C_{22}$), for example the natural Na or K salts of oleic or stearic acids, or of natural mixtures of fatty acids which can be obtained, inter alia, from coconut oil or tallow oil. Other surfactants which may be mentioned are fatty acid methyltaurine salts, and modified and non-modified phospholipids.

However, more frequently used surfactants are so-called synthetic surfactants, in particular fatty sulfonates, fatty sulfates, sulfonated benzimidazole derivatives or alkylarylsulfonates.

The fatty sulfonates and fatty sulfates are usually present in the form of alkali metal salts, alkaline earth metal salts or optionally substituted ammonium salts and generally have an alkyl radical containing 8 to 22 C atoms, alkyl also encompassing the alkyl moiety of acyl radicals. Examples are the Na or Ca salt of ligninsulfonic acid, of dodecylsulfuric ester and sulfonic acids of fatty alcohol/ethylene oxide adducts. The sulfonated benzimidazole derivatives preferably contain two sulfonyl groups and one fatty acid radical containing about 8 to 22 C atoms. Alkylarylsulfonates are, for example, the Na, Ca or triethanolamine salts of dodecylbenzenesulfonic acid, of dibutylnaphtha-lenesulfonic acid or of a naphthalenesulfonic acid/formaldehyde condensation product.

The non-ionic surfactants are mainly chosen from amongst the polyglycol ether derivatives of aliphatic or cycloaliphatic alcohols, saturated or unsaturated fatty acids and alkylphenols which can contain 3 to 30 glycol ether groups and 8 to 20 C atoms in the (aliphatic) hydrocarbon radical and 6 to 18 C atoms in the alkyl radical. Other suitable non-ionic surfactants are the water-soluble polyethyleneoxy-adducts onto polypropylene glycol and alkyl polypropylene glycol with 1 to 10 C atoms in the alkyl chain, which adducts contain 20 to 250 ethylene glycol ether groups and 10 to 100 propylene ether groups. The compounds which have been mentioned customarily contain 1 to 5 ethylene units per propylene glycol unit.

The following may be mentioned as examples of non-ionic surfactants: nonylphenol polyethoxyethanols, castor oil polyglycol ethers, polypropylene/polyethylene oxide adducts, tributylphenoxy-polyethoxy-ethanol, polyethyleneglycol and octylphenoxy-polyethoxyethanol. Moreover, fatty acid esters of polyoxyethylene-sorbitan, such as polyoxyethylene sorbitan trioleate, are also suitable.

The cationic surfactants are mainly quaternary ammonium salts which contain at least one alkyl radical having 8 to 22 C atoms as the N-substituent and which have lower, optionally halogenated alkyl radicals, benzyl radicals or lower hydroxyalkyl radicals as further substituents. The salts are mainly present in the form of halides, methylsulfates or ethylsulfates, for example stearyltrimethylammonium chloride or benzyldi-(2-chloroethyl)-ethylammonium bromide.

When preparing the inventive spontaneously dispersible concentrates, special preference is given on the one hand to phosphoric acid ester tensides, such as:
Tristyrylphenolpolyoxyethylene-18-mono/dimethyl-phosphoric-acid-ester

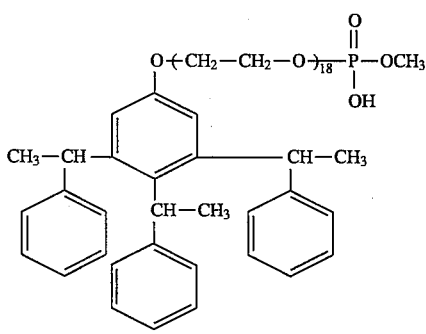

(Soprophor® FL, Rhône-Poulenc);

Nonylphenol-10-polyoxyethylene-mono/dimethylphosphoric-acid-ester
(Diphasol200 3873, CIBA-GEIGY); or the identical Sermul® EA 188 (SERVO)

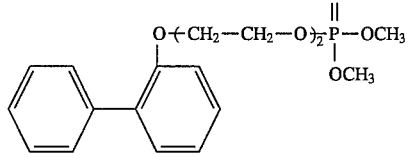

(Tensid 508, CIBA-GEIGY);

Tinovetin® JU (CIBA-GEIGY), a hydroxybiphenyl-10-ethoxy-phosphoric acid ester

Butyl-mono-4-ethoxy-phosphoric acid ester (Zerostat® AT, CIBA-GEIGY), and

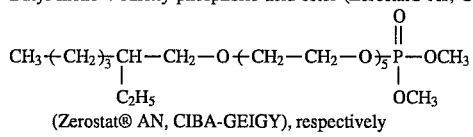

(Zerostat® AN, CIBA-GEIGY), respectively and on the other hand to betain compounds, i.e. amphoteric, salt- and waterfree imidazole derivatives, such as e.g.

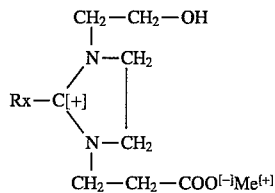

in which Me[+] stands for hydrogen, alkali and/or earth alkali atoms, and $R_x$ for a $C_1$ to $C_{32}$ alkyl or $C_2$ to $C_{32}$ alkenyl group
or multifunctional glucose derivatives such as Glucate® SS (methyl glucose sesquistearate) and Glucamate® SSE-20 (PEG-20 methyl glucose sesquistearate) both available from (Amerchol)

The following compounds may be employed as the pharmaceutically acceptable solvent which acts as the hydrotropic, or coemulsifier, for example: esters of an aliphatic alcohol ($C_3$ to $C_{18}$) with an aliphatic carboxylic acid ($C_{10}$ to $C_{22}$), such as isopropyl laurate, hexyl laurate, decyl laurate, isopropyl myristate and lauryl myristate; hydrocarbons having a straight carbon chain ($C_{12}$ to $C_{32}$) which is substituted by 6 to 16 methyl groups and which can have up to 6 double bonds, examples which may be mentioned being terpenes, such as polymethylbutanes and polymethylbutenes.

Monoesters of ethylene glycol or propylene glycol with an aliphatic carboxylic acid ($C_6$ to $C_{22}$), such as propylene glycol monolaurate and propylene glycol monomyristate.

Esters of an aliphatic alcohol ($C_{12}$ to $C_{22}$) with lactic acid, such as, for example, myristyl lactate or, preferably, lauryl lactate. Monoesters or diesters of glycerol with an aliphatic carboxylic acid ($C_6$ to $C_{22}$), such as, for example, glyceryl caprylate or Miglyol® 812 neutral oil (oleum neutrale).

Esters of a poly(2–7)ethylene glycol glycerolether having at least one free hydroxyl group with an aliphatic carboxylic acid ($C_6$ to $C_{22}$), such as, for example, aliphatic alcohols ($C_{12}$ to $C_{22}$), thus, inter alia, dodecanol, tetradodecanol, oleyl alcohol, 2-hexyldecanol and 2-octyl-decanol.

Esters containing at least one free hydroxyl group, of poly-(2–10)glycol with an aliphatic carboxylic acid ($C_6$ to $C_{22}$), monoethers of a polyethylene glycol with an aliphatic alcohol ($C_{12}$ to $C_{18}$), such as, for example, polyoxyethylene-($C_{10}$) octylether.

Heterocyclic compounds such as 1-methyl-2-pyrrolidon.

Before their application in the spontaneously dispersible concentrates all technical tensides have been cleaned by filtration or by chromatography over aluminum-oxide with an inert solvent as eluent, such as tetrahydrofurane, ethylalcohol or dichloromethane.

Suitable additives for the spontaneously dispersible concentrates according to the invention are vitamins and provitamins [such as, for example, vitamin A (retinoic acids), retinol, carotenes, tocopherols], and also free fatty acids, such as: valeric acid, isovaleric acid, sorbic acid, isocaproic acid, pelargonic acid, lauric acid, myristic acid, palmitic acid, stearic acid, arachidic acid, behenic acid, hexacosanoic acid, octacosanoic acid, pentadecanoic acid, decenylic acid, undecylenic acid, dodecenylic acid, oleic acid, linoleic acid, linolenic acid, arachidonic acid, erucic acid, etc.

The daily dose required for pharmaceutical administration is 0.001 to 25 mg/kg of body weight, if possible split into 2–3 individual doses. For this purpose, the new sterol esters and terpene esters, or the spontaneously dispersible concentrates with these compounds, can be incorporated into the conventional pharmaceutical preparations and dosage forms, such as coated tablets, tablets, capsules, powders, granules, pellets, solutions, ampuls, emulsions, creams or suppositories together with the customary excipients and/or diluents and stabilizers.

The active substances or mixtures of active substances which form the subject-matter of the invention, and the spontaneously dispersible concentrates which contain these active substances or mixtures of active substances, can be administered to humans orally, by injection (intravenously, subcutaneously or intramuscularly) or in other ways. If they are presented as solid dosage forms for oral administration, this can be in the form of tablets, granules, pellets, powders or capsules, etc. The preparations can contain additives, for example a pharma-ceutical excipient, such as a saccharide or cellulose base, a binder, such as starch paste or methylcellulose, a filler, or a disintegrant, etc., with additives being employed which are customarily used in the preparation of medicinal or pharmaceutical formulations. When the active substances or mixtures of active substances according to the invention are administered orally in the form of liquid dosage forms, they can be present in any form selected from amongst aqueous preparations for internal use, from suspensions, emulsions and syrups, etc., and they can also be present in the form of dried preparations which are dissolved or emulsified prior to use.

When the active substances or mixtures of active substances according to the invention are processed in the form of aqueous solutions, suspensions or oily or aqueous emulsions, preferably microemulsions, from the spontaneously dispersible concentrates according to the invention, they can also be injected. However, it is customary to prepare the injection solutions shortly before administration, by dissolving or suspending the extracts or concentrates in aqueous, liquid media, such as sterile water or physiological sodium chloride solution or glucose solution.

If required, conventionally used solvents, stabilizers, preservatives and additives for the preparation of isotonic solutions can be added to a preparation for injection. The preparations for injection obtained in this manner are administered intravenously, intramuscularly, subcutaneously or in any other suitable way.

The present invention also relates to pharmaceutical preparations which contain the active substances, or mixtures of active substances, or the spontaneously dispersible concentrates, which have been above described, for controlling the growth of tumour cells. The pharmaceutical preparations according to the invention are those which can be used for enteral (such as oral or rectal) or for parenteral or topical administration to warm-blooded animals, which preparations contain the spontaneously dispersible concentrate on its own or together with a pharmaceutically acceptable excipient.

The dosage of the concentrates according to the invention depends on the warm-blooded species, on the age and on the individual condition, and on the mode of administration. For example, doses in the range of about 0.1–50 mg/kg of body weight are administered subcutaneously, and doses in the range of 0.05–5 mg/kg of body weight are administered intraperitoneally to warm-blooded animals having a low body weight, such as, for example, mice, rats and hamsters, to achieve an effect of tumour cell destruction.

The oral and rectal forms of the novel pharmaceutical preparations contain between 1 and 95%, preferably between 10 and 95%, and in particular between 20 and 95%, of the spontaneously dispersible concentrate according to the invention. For example, they can be present in unit-type dosage forms, i.e., as coated tablets, micropellets, tablets, suppositories or ampuls and, in particular, as capsules.

Suitable pharmaceutically acceptable excipients for the oral forms are mainly fillers, such as sugars (for example lactose, sucrose, mannitol or sorbitol), cellulose preparations and/or calcium phosphates (for example tricalcium phosphate or calcium hydrogen phosphate), furthermore binders, such as starch paste, with the use of, inter alia, corn starch, wheat starch, rice starch or potato starch, gelatine, tragacanth, methylcellulose, hydroxy-methylcellulose, sodium carboxy-methylcellulose and/or polyvinylpyrrolidone and/or disintegrants (if desired), such as the above mentioned starches, furthermore carboxy-methyl starch, crosslinked polyvinylpyrrolidone, agar, alginic acid or a salt thereof, for example sodium alginate. Examples of suitable flow-control agents are the polyethylene glycols Nos. 200 to 600 and above.

The gelatine capsules, which are still the preferred dosage form for hu-mans, are provided with suitable coatings, concentrated sugar solutions [which can optionally contain gum arabic, talc, polyvinylpyrrolidone, polyethylene glycol and/or titanium dioxide], lacquer solutions (aqueous or those which have been prepared using organic solvents), or enteric coatings of solutions of suitable cellulose preparations, such as microcrystalline cellulose (Avicel®), acetyl-cellulose phthalate, hydroxy-methylcellulose-phthalate, Metolose®, AQOAT® or a copolymer, such as Eudragit® L 30 D, being used, inter alia.

Pharmaceutical dosage forms for oral use which are particularly suitable according to the invention are two-piece gelatine capsules with a plasticizer, such as glycerol or sorbitol. The soft-gelatine or hard-gelatine capsules and the capsules made of AQOAT® hydroxypropyl methylcellulose respectively can contain the spontaneously dispersible concentrate according to the invention as a mixture with fillers, such as lactose, binders, such as starch, and/or glidants, such as talc or magnesium stearate, and, if appropriate, together with stabilizers and antioxidants, such as, for example, α-, β- or γ-tocopherol. It may be expedient to employ suitable liquids, such as liquid polyethylene glycols Nos. 200 to 600 as diluents, to which stabilizers and antioxidants can also be added.

For parenteral administration, distilled water is added to the concentrates according to the invention. To the aqueous microemulsion for injection which then forms, there can be added viscosity-increasing substances, for example Na-carboxymethylcellulose, sorbitol, mannitol and/or dextran, and if appro-priate also stabilizers and antioxidants.

The pharmaceutical preparations for parenteral administration preferably contain between 0.1 and 60%, especially between 1 and 40%, of the spontaneously dispersible concentrate according to the invention. Suitable preparations for topical use, which are particularly suitable for the prophylaxis and the treatment of cancers of the skin, are, for example, creams, ointments, pastes, foams, tinctures and solutions, which contain between 0.001 and 70% of the concentrate according to the invention.

Oily bases which are used for creams and oil-in-water emulsions which contain more than 50% water, are mainly fatty alcohols, for example lauryl alcohol, cetyl alcohol or stearyl alcohol, waxes of liquid to solid consistency, for example isopropyl myristate, wool wax or beeswax and/or hydrocarbons, such as, for example, petroleum jelly (petrolatum) or paraffin oil. Substances which are mainly suitable for emulsifying these oily bases are surface-active, pharmaceutically acceptable substances having predominantly hydrophilic properties, such as, for example, non-ionic emulsifiers, in particular fatty acid esters of polyalcohols or ethylene oxide adducts (such as polyglycerol fatty acid esters or polyethylene sorbitan fatty acid esters) having an HLB value of less than 8. Additives which are added to the water phase are, inter alia, agents which prevent desiccation of the creams, for example polyalcohols, such as glycerol, sorbitol, propylene glycol and/or polyethylene glycols Nos. 200 to 600, and furthermore preservatives, odor-imparting substances, etc.

Ointments are water-in-oil emulsions which contain up to 70%, but preferably between 20 and 50%, water or aqueous phases.

Substances which are suitable as the lipid phase are mainly hydrocarbons, for example petroleum jelly, paraffin oil and/or solid paraffins, which contain hydroxy compounds suitable for improving the water-binding capacity, for example fatty alcohols or esters, such as cetyl alcohol or wool wax alcohols. In some cases, emulsifiers having an HLB-value of 8 to 16, such as, for example, sorbitan fatty acid esters (such as sorbitan isostearol) are also added. Additives which are added to the water phase are, inter alia, humectants, such as polyalcohols (glycerol, propylene glycol, sorbitol and/or polyethylene glycols No. 200, 400, 600); and furthermore pre-servatives, odor-imparting substances, etc.

Fatty ointments are anhydrous and chiefly contain hydrocarbons as the base, for example paraffin, petroleum jelly and/or liquid paraffins; moreover natural or partially-synthetic fats, such as, for example, coconut fatty acid triglyceride, furthermore: fatty acid partial esters of glycerol, such as, for example, the fatty alcohols, emulsifiers and/or additives which increase the water-absorption capacity, all of which have been mentioned in connection with the ointments.

Pastes are creams and ointments containing powder constituents which absorb secretions, such as, for example, metal oxides (such as titanium oxide or zinc oxide), and furthermore talc and/or aluminum silicates whose task it is to bind any moisture or discharge which may be present.

Foams are administered from pressurized containers and are oil-in-water emulsions of the spontaneously dispersible concentrates according to the invention which are present in aerosol form, with halogenated hydrocarbons (such as, for example, lower chloro-fluoroalkanes; such as dichlorodifluoromethane and dichlorotetrafluorethane) being added as propellants. Other substances which may be added are the customary additives, such as preservatives, etc.

The present invention also relates to the use of the active substances, mixtures of active substances and spontaneously emulsifiable concentrates according to the invention for inhibiting the growth of tumour cells or as prophylactic agents against oncoses in humans and animals, administration preferably being carried out in the dosage forms which correspond to the pharmaceutical preparations described above.

PROCESSING EXAMPLES FOR INVENTIVE BIOTENSIDE ESTERS

1. Process for the Preparation of Azafrin Phytyl Ester

To 80 mg of azafrin [compound according to formula (XXII); synthesis cf. Helv. Chim. Acta 58 (1975) 1722–1727 and Helv. Chim. Acta 65 (1982) 353–354] in 50 ml chloroform 65 mg N,N'-carbonyl-diimidazol are being added. The reaction mixture is left standing for 12 hours at 20° C.; then 30 mg phytol (3,7,11,15-Tetramethyl-2-hexadecen-1-ol; 33% cis and 67% trans) are added. After a further 12 hours at 30° C., the solvent is being distilled off and the residue taken up in ethyl acetate. This solution is washed once with $\frac{1}{10}$N hydrochloric acid and once with $\frac{1}{10}$N sodium hydroxide and then the solvent is distilled off. The residue is chromatographed on a silicagel column; eluent: n-hexane/ethyl acetate 9:1.

One obtains the azafrin phytyl ester, having a UV-absorption ot λmax. 233,0 nm (dichloromethane), a refractory Index (RI) n 20/D of 1,47714 and a $R_f$-Value of 0,92 (TLC).

2. Preparation of All-trans Retinoic Acid Phytyl Ester

To 600 mg all-trans retinoic acid and 50 mg dimethyl formamide in 50 ml toluene at 5° C., 360 mg oxalyl chloride are being added dropwise in 30 ml toluene. After standing for 4 hours at 20° C. one half of the solvent is distilled off in vacuo. To the residue 300 mg phytol (3,7,11,15-Tetramethyl-2-hexadecen-1-ol; 33% cis and 67% trans) and 50 mg p-dimethylaminopyridin in 30 ml toluene are added. The reaction solution is refluxed during 2 hours at 60° to 70° C. Subsequently the solvent is distilled off on a Rotavapor. The residue is being chromatographed on a silicagel column with hexane/ethyl acetate (9:1).

One obtains the all trans retinoic acid phytyl ester, having a UV-absorption of λmax. 360,5 nm (dichloromethane); a refractory index (RI) n 20/D of 1,49266 and $R_f$-values of 0,67; 0,71 and 0,83.

| | | |
|---|---|---|
| IR | 2929 cm⁻¹ | ν (CH) |
| | 2867 cm⁻¹ | ν (CH) |
| | 1738 cm⁻¹ | ν (C=O) ester |
| | 1701 cm⁻¹ | ν (C=O) ester |
| | 1583 cm⁻¹ | ν (C=C) a.t.retinate |
| | 1462 cm⁻¹ | δ (CH) |
| | 1378 cm⁻¹ | δ (CH₃) |
| | 1152 cm⁻¹ | ν (C—O) ester |
| | 969 cm⁻¹ | δ (CH) trans (C—C) |
| FT RAMAN | 1585 cm⁻¹ | (C=C) |
| C13 NMR | Ester binding α (CH₂) phytol at 63 ppm | |

3. Preparation of All Trans Retinoic Acid Farnesyl Ester

To 600 mg all-trans retinoic acid in 50 ml toluene at 5° C. 360 mg oxalyl chloride in 30 ml toluene are being added dropwise. After standing for 10 hours at 20° C. one half of the solvent is being distilled off in vacuo. The remaining solution is being added dropwise during one half hour to a solution consisting of 220 mg 3,7,11-trimethyl (-2,6,10-dodecatrien-1-ol) [mixture of trans-trans and cis-trans farnesol], 150 mg dimethyl formamide in 40 ml toluene under continuous stirring at 20° C.

Subsequently the reaction solution is refluxed during 2 hours at 60° to 70° C. Then the solvent is being distilled off in vacuo, and the residue is chromatographed with hexane/ethyl acetate (9:1) as eluent.

One obtains the all trans retinoic acid farnesyl ester having a UV-aborption λmax. of 366,5 nm (dichloromethane), a refractory index (RI) n 20/D of 1,50364 and a $R_f$-Value of 0.89.

In an analogous manner the following biotenside esters can also be obtained:

| | |
|---|---|
| All trans retinoic acid phytyl ester | UV λmax.360,5 nm |
| | RI 1,49266 |
| | $R_f$-Values 0,67; 0,71 and 0,83 |
| All trans retinoic acic citronellyl ester | UV λmax.365,5 nm |
| | RI 1,51362 |
| | $R_f$ 0,79 and 0,88 |
| All trans-retinoic acid geranyl ester | |

4. Preparation of Caprylic Acid Phytyl Ester

To a solution of 3 g phytol (3,7,11,15-Tetramethyl-2-hexadecen-1-ol), 1,5 g dimethyl formamide in 50 ml toluene is being added dropwise during one half hour a solution consisting of 2 g caprylic acid chloride (excess) in 25 ml toluene at 20° C.

The reaction solution is subsequently heated to 60° to 70° C. and refluxed for 2 hours. After distilling off the solvent in vacuo, the residue is taken up on a silicagel column and chromatographed with hexane/ethyl acetate (9:1) as eluent.

| | | |
|---|---|---|
| One obtains the caprylic acid phytyl ester | UV | λmax. 240,0 nm |
| | RI | 1,46328 |

In similar manner, the following biotenside esters can also be obtained:

| | | |
|---|---|---|
| Pivalic acid phytyl ester | UV | λmax. 236,8 nm |
| | RI | 1,45750 |

| | | |
|---|---|---|
| Pelargonic acid phytyl ester | UV | λmax. 231,8 nm |
| | RI | 1,46198 |
| Crotonic acid phytyl ester | UV | λmax. 242,0 nm |
| | RI | 1,46328 |
| 10-Undecylenic acid phytyl ester | | |
| Lauric acid phytyl ester | | |
| Palmitic acid phytyl ester | UV | λmax. 232,8 nm |
| | RI | 1,46182 |
| Oleic acid phytyl ester | UV | λmax. 232,6 nm |
| | RI | 1,46586 |
| Palmitic acid farnesyl ester | | |
| Oleic acid farnesyl ester | | |
| Palmitic acid citronellyl ester | | |
| Oleic acid citronellyl ester | | |
| Palmitic acid geranyl ester | | |
| Oleic acid geranyl ester | | |

5. Preparation of Azelaic Acid-bis-phytyl Ester

To a solution of 6 g phytol (3,7,11,15-Tetramethyl-2-hexadecen-1-ol), and 2 g of dimethyl formamide in 50 ml toluene one adds dropwise during one half hour a solution constisting of 2,5 g azelaic acid dichloride (excess) in 25 ml toluene at 20° C.

The reaction mixture is subsequently heated and refluxed at 70° C. for 3 hours. After distilling off the solvent in vacuo on a Rotavapor, the residue is taken up on a silicagel column and chromatographed with hexane/ethyl acetate (9:1) as eluent. One obtains the azelaic acid bis-phytyl ester. UV λmax. 233,0 nm (dichloromethane), RI 1,46444, $R_f$ 0,89

In an analogous manner, the following biotenside double esters can also be obtained:

| | | |
|---|---|---|
| Sebacic acid bis-phytyl ester | UV | λmax. 232,6 nm |
| | RI | 1,46722 |
| Glutaric acid bis-phytyl ester | UV | λmax. 240,0 nm |
| | RI | 1,46622 |
| Fumaric acid bis-phytyl ester | UV | λmax. 241,6 nm |
| | RI | 1,46884 |
| Malonic acid bis-phytyl ester | UV | λmax. 236,8 nm |
| | RI | 1,46588 |
| Succinic acid bis-phytyl | IR | 2929 cm$^{-1}$ ν (CH) |
| | | 2868 cm$^{-1}$ ν (CH) |
| | | 1730 cm$^{-1}$ ν C=O) ester |
| | | 1385 cm$^{-1}$ δ (CH$_3$) |
| | | 1161 cm$^{-1}$ ν (C—O) ester |
| Azelaic acid bis-geranyl ester | | |
| Azelaic acid bis-farnesyl ester | | |
| Azelaic acid bis-citronellyl ester | | |
| Succinic acid ethyl-phytyl ester | | |
| Succinic acid methyl-phytyl ester | UV | λmax. 240,0 nm |
| | RI | 1,46024 |
| Glutaric acid ethyl-phytyl ester | UV | λmax. 240,0 nm |
| | RI | 1,46310 |
| Glutaric acid methyl-phytylester | | |
| Azelaic acid ethyl-phytyl ester | | |
| Azelaic acid methyl-phytyl ester | | |

COMPOSITION EXAMPLES of inventive, spontaneously dispersible CONCENTRATES containing the biotenside esters according to formulae (I) to (VII) as SOLVENTS and HYDROTROPIC AGENTS (Coemulgators).

a) 0,5 to 30% by weight of one or several therapeutic or cosmetic agents 1 to 40% by weight of one or several of the inventive biotenside esters according to formulae (I) to (VII)

0 to 45% by weight of a phosphoric acid ester tenside, such as e.g. DIPHASOL® 3873 (CIBA-GEIGY), or the identical SERMUL® EA 188 (SERVO), Tenside 508 (CIBA-GEIGY), ZEROSTAT® AN or AT (CIBA-GEIGY), TINOVETIN® JU (CIBA-GEIGY), SOPROPHOR® FL (Rhône-Poulenc)

5 to 90% by weight of INVADIN® JFC 800% (CIBA-GEIGY)

Invadin® JFC 800% (CIBA-GEIGY) is a pharmaceutically acceptable tert. octyl-phenyl-polyoxyethylene-ether having 9 to 10 oxyethylene groups.

Diphasol® 3873 (CIBA-GEIGY) and the identical Sermul® EA 188 (SERVO) ist a combination emulgator, consisting of 50% each of the following compounds with formulae:

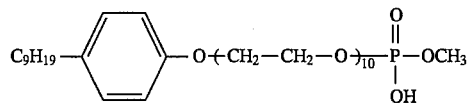

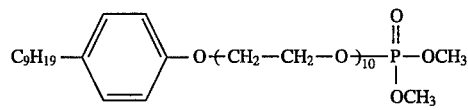

DIPHASOL® 3873 (CIBA GEIGY)

Tenside 508 (CIBA-GEIGY) is an emulgator of formula:

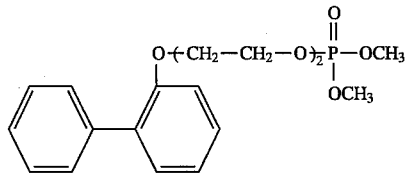

(Tensid 508, CIBA-GEIGY);

Tinovetin® JU (CIBA-GEIGY), is a hydroxybiphenyl-10-ethoxy-phosphoric acid ester;

Zerostat® AT (CIBA-GEIGY) is a butyl-mono-4-ethoxy-phosphoric acid ester;

Zerostat® AN (CIBA-GEIGY) is an emulgator of formula:

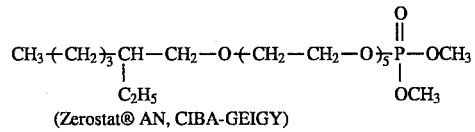

(Zerostat® AN, CIBA-GEIGY)

Soprophor® FL (Rhône-Poulenc) is a tristyrylphenol-polyoxyethylene 18-phosphoric acid ester of formula:

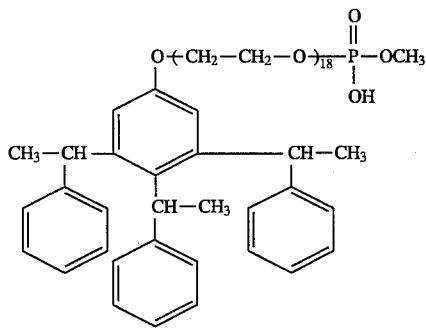

(SOPROPHOR FL (Rhône-Poulenc);

b) 0,5 to 30% by weight of one or several of therapeutic or cosmetic agents 1 to 40% by weight of one or several of the inventive biotenside esters according to formulae (I) to (VII)

0 to 45% by weight of a betain compound, i.e. an amphoteric, salt- and waterfree imidazole derivative of the formula:

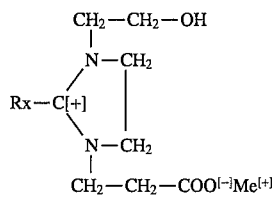

in which Me[+] designates hydrogen, alkali- and earth alkali atomes and $R_x$ stands for a $C_1$ to $C_{32}$ alkyl or $C_2$ to $C_{32}$ alkenyl group, naming explicitely as specific example the product Amphonyl® CAA (Oranienburger Chemikalien A.G.) [Imidazole derivative produced on the basis of coconut fat acids].

c) 10% by weight of an oily antitumor agent, selected from the enumeration given on pages 19ss, such as, e.g., 10-Undecenyl-Ergocalciferyl-Ester 20% by weight of an inventive biotenside ester according to formulae (I) to (VII)

35% by weight of Invadin® JFC 800%

35% by weight of Diphasol® 3873 d) 5% by weight of a crystalline antitumour agent, selected from the enumeration given on pages 19ss., such as, e.g., 10-Undecenyl-3-Ergosteryl ester 15% by weight of an inventive biotenside ester according to formulae (I) to (VII)

40% by weight of Invadin® JFC 800%

40% by weight of Soprophor® FL or Amphonyl® C-AA

COMPARATIVE ASSAYS WITH DIFFERENT COMPOSITIONS OF THE TEST CONCENTRATE

BASIS:

10% by weight of cholecalciol-10-undecenoate (C 11:1-$D_3$)

10% by weight of undecenyl citronellyl ester (C 11:1—CITRONELLYL ESTER)

80% by weight of TENSIDES MIXTURE No. 1 to 8

Testing an aqueous micro-, and macroemulsion resp. 1:1'000 (=1'000 ppm active substance content) in-vitro with Py6-cells (Virus transformed mouse-fibroblasts)

| CONCENTRATES containing | | Surface tension (Plate method) |
|---|---|---|
| No. 1 | 50:50 Invadin JFC 800%/Soprophor FL | 33,8 mN/m |
| No. 2 | 60:40 Invadin JFC 800%/Amphonyl CAA | 30,6 mN/m |
| No. 3 | 50:50 Invadin JFC 800%/Diphasol 3873 | 31,6 mN/m |
| No. 4 | 100% Cremophor EL | 36,9 mN/m |
| No. 5 | 50:50 Invadin JFC 800%/Glucate SS | 31,7 mN/m |
| No. 6 | 50:50 Invadin JFC 800%/Phosal 75 SA | 28,3 mN/m |
| No. 7 | 50:50 Invadin JFC 800%/Phospholipon 80 | 32,6 mN/m |
| No. 8 | 100% Phospholan PMP 9 | 31,7 mN/m |

| CYTOTOXICITY on Py6-cells: highest active dilution 1: | | | |
|---|---|---|---|
| CONCENTRATE | 24 h | 48 h | 72 h |
| No.1 | 3,2 Mio. | 12,8 Mio. | 12,8 Mio. |
| No. 2 | 3,2 Mio. | 12,8 Mio. | 12,8 Mio. |
| No. 3 | 3,2 Mio- | 12,8 Mio. | 12,8 Mio. |

| CYTOTOXICITY on Py6-cells: highest active dilution 1: | | | |
|---|---|---|---|
| CONCENTRATE | 24 h | 48 h | 72 h |
| No. 4 | 400'000 | 800'000 | 800'000 |
| No. 5 | 12,8 Mio. | 25,6 Mio. | 25,6 Mio. |
| No. 6 | 400'000 | 400'000 | 400'000 |
| No. 7 | 6,4 Mio. | 6,4 Mio. | 12,8 Mio. |
| No. 8 | 1,6 Mio- | 3,2 Mio. | 3,2 Mio- |

EXAMPLE of the Pharmaceutical Production of a System's Preparation Containing the INVENTIVE MARIGENOL® CONCENTRATES in the Form of "Multiple Units".

| a) Granulation (granules and pellets) | |
|---|---|
| Metolose ® 90 SH-4000 (Shin-Etsu Chemical) | 90.0 g |
| Avicel ® PH-101 | 80.3 g |
| Inventive MARIGENOL ®-CONCENTRATE | 139.4 g |
| Aerosil ® 200 | 80.3 g |
| Σ | 390.0 g |

Granulation in the high speed mixer or the fluidized bed, with the addition of 110 g ethanol, crushing, sieving on a 18 to 42 mesh screen, drying for 24 h at 40 ° C.

b) MSR- and sustained-release coating in the fluidized bed with AQOAT® AS-HG (Shin-Etsu Chemical) and using talc.

c) Composition of the finished granules or micropellets:

| Core material | 44% by weight |
|---|---|
| Inventive MARIGENOL ®-CONCENTRATE | 25% by weight |
| Enteric coating | 31% by weight |
| Σ | 100% by weight |

N.B. The pellets or granules according to a) can also be filled without subsequent coating into capsules which are made of AQOAT® (HPMC-AS-M or HPMC-AS-N), have been sealed with acetone/ethanol 1:1 and can thus perform the functions of pH-control and slow-release. This new form of administration is preferred for the inventive concentrates on account of their enhanced stability.

P.S.: MARIGENOL® is a registered trade-mark (™) of MARIGEN S. A., RIEHEN

DETERMINATION OF THE HYDRODYNAMIC RADIUS OF THE MICELLES IN MICROEMULSIONS, WHICH HAVE BEEN GENERATED WITH INVENTIVE MARIGENOL®-CONCENTRATES

The following inventive CONCENTRATES were diluted with distilled water at the ratio 1:1000 (calculated on the content of active substance):

a) 10% by weight of 10-undecenylic acid ergocalciferyl ester

20% by weight of azelaic acid bis citronellyl ester

35% by weight of Invadin® JFC 800%

35% by weight of Diphasol® 3873 b) 5% by weight of 10-undecenylic acid ergosteryl ester

15% by weight of 10-undecenylic acid phytyl ester

40% by weight of Invadin® JFC 800%

40% by weight of Diphasol® 3873

At the Institute for Polymer Chemistry of the Swiss Federal Institute of Technology (E.T.H.), Zürich (Prof. Dr. Pierluigi LUISI and Prof. Dr. Peter SCHURTENBERGER)

the generated microemulsions have been subjected to ultrasensitive light scattering measurements. The result was that the HYDRODYNAMIC RADIUS OF THE MICELLES FORMED IN THE TESTED MICROEMULSIONS WAS 1 TO 1,2 NM.

Examples Illustrating the Enhanced Bioavailability/therapeutic Efficacy of Concentrates Which Contain As Solvents the Inventive Terpane Esters Cytotoxicity on Py6-Cells (Polyoma-transformed 3T3-mouse cells; fibroblasts)

|  | Greatest cytotoxic dilution | |
| --- | --- | --- |
|  | 24 h Exp. | 48 h Exp. |
| β-Estradiol - Concentrate 1) | 1:327'680 | 1:655'360 |

N.B.:
1) Concentrate formed with
   3,2% by weight of β-Estradiol [1,3,5-estradiol-3,17β-diol]
   32,2% by weight of fumaric acid phytyl-diester
   64,5% by weight of Invadin JFC 800%

|  | Greatest Cytotoxic dilution | |
| --- | --- | --- |
|  | 24 h Exp. | 48 h Exp. |
| C 11:1 - D₃-concentrate purum, diluted with DMSO | 1:2'560 | 1:2'560 |
| C 11:1 - D₃-concentrate 2) diluted with distilled water | 1:512'000 | 1:512'000 |

N.B.:
2) Concentrate containing
   10% by weight of undecenylic acid cholecalciferyl ester as active substance
   45% by weight of azelaic acid phytyl-diester
   45% by weight of Invadin JFC 800%

We claim:

1. A spontaneously dispersible concentrate formulated by using as a hydrotropic agent or coemulgator 0.001 to 50% by weight of a biotenside ester or a combination of biotenside esters having one of the following formulae (I) to (VII):

$$R_1OCO-(CH_2)_m-OCOR_2 \quad (I)$$

$$R_1OCO-C=CH-OCOR_2 \quad (II)$$
$$\phantom{R_1OCO-}|$$
$$\phantom{R_1OCO-}R_3$$

(III)

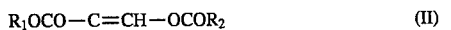
(IV)

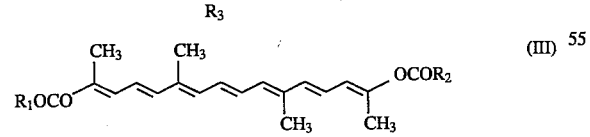
(V)

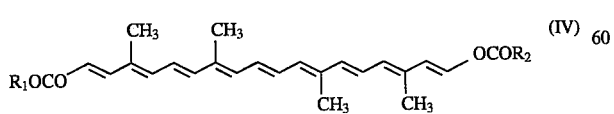
(VI)

$$R_5-OCOR_1 \quad (VII)$$

wherein
$R_1$ is citronellyl, geranyl, farnesyl, phytyl or isophytyl;
$R_2$ is chlorine, methyl, citronellyl, geranyl, farnesyl, phytyl or isophytyl;
$R_3$ is hydrogen;
$R_5$ is a $C_{8-22}$ alkyl, $C_{8-22}$ alkenyl, or $C_{8-22}$ alkapolyene group;
n is 1 or 2;
o is 1 or 2;
p is 1; and
$R_4$ is

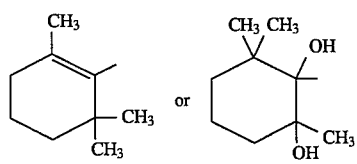

said concentrate further comprising:
0.001 to 30% by weight of a therapeutic agent, a cosmetic agent, or a combination thereof,
0.001 to 90% by weight of a pharmaceutically acceptable tenside or combination of tensides,
up to 10% by weight of a vitamin or provitamin,
up to 10% by weight of a free fatty acid, excipient, diluent, or a combination thereof.

2. A spontaneously dispersible concentrate as claimed in claim 1, wherein the concentrate comprises
10 to 50% by weight of a biotenside ester or a combination of biotenside esters according to claim 1, said concentrate further comprising:
0.5 to 30% by weight of a therapeutic agent, a cosmetic agent, or a combination thereof,
up to 45% by weight of a phosphoric acid ester tenside or a tenside of the formula

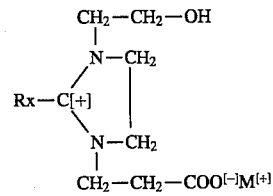

wherein M is hydrogen, an alkali or alkali earth atom and $R_x$ is a $C_{1-32}$ alkyl, $C_{2-32}$ alkenyl or a multifunctional glucose derivative selected from the group consisting of methyl glucose sesquistearate and PEG-20 methyl glucose sesquistearate, and
up to 45% by weight of a pharmaceutically acceptable tert.octyl-phenyl-polyoxyethylene ether having 9 or 10 oxyethylene groups.

3. A spontaneously dispersible concentrate as claimed in claim 2, wherein the phosphoric acid ester tenside is a mixture of
tristyrylphenolpolyoxyethylene-18-monomethyl-phosphoric acid ester, and tristyrylphenolpolyoxyethylene-18-di-phosphoric acid ester, a mixture of nonylphenol-10-polyoxyethylene-monomethylphosphoric acid ester, and nonylphenol-10-polyoxyethylene-dimethylphosphoric acid ester, hydroxybiphenyl-10-ethoxy-phosphoric acid ester or butyl-mono-4-ethoxy-phosphoric acid ester and wherein the multifunctional glucose derivative is methyl glucose sesquistearate or PEG-20 methyl glucose sesquistearate.

4. A spontaneously dispersible concentrate as claimed in claim 1, wherein the concentrate comprises
  20% by weight of a biotenside ester or a combination of biotenside esters according to claim 1, said concentrate further comprising:
    10% by weight of an oily anti-tumor agent,
    35% by weight of a pharmaceutically acceptable tert.octyl-phenyl-polyoxyethylene ether having 9 to 10 oxyethylene groups, and
    35% by weight of a phosphoric acid ester tenside or a tenside of the formula

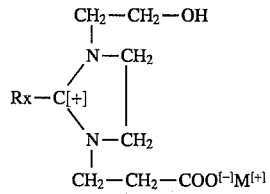

wherein M is hydrogen, an alkali or alkali earth atom and $R_x$ is a $C_{1-32}$ alkyl, $C_{2-32}$ alkenyl or a multifunctional glucose derivative selected from the group consisting of methyl glucose sesquistearate and PEG-20 methyl glucose sesquistearate.

5. A spontaneously dispersible concentrate as claimed in claim 4, wherein the phosphoric acid ester tenside is a mixture of
  tristyrylphenolpolyoxyethylene-18-monomethyl-phosphoric acid ester, and
  tristyrylphenolpolyoxyethylene-18-dimethyl-phosphoric acid ester, a mixture of 6. A spontaneously dispersible concentrate as claimed in claim 1, wherein the concentrate comprises
  15% by weight of a biotenside ester or a combination of biotenside esters according to claim 1, said concentrate further comprising:
    0.5 to 30% by weight of a therapeutic agent, a cosmetic agent, or a combination thereof,
    up to 40% by weight of a pharmaceutically acceptable tert.octyl-phenyl-polyoxyethylene ether having 9 to 10 oxyethylene groups, and
    up to 40% by weight of a phosphoric acid ester tenside.

7. A spontaneously dispersible concentrate as claimed in claim 6, wherein the phosphoric acid ester tenside is a mixture of
  tristyrylphenolpolyoxyethylene-18-monomethyl-phosphoric acid ester, and
  tristyrylphenolpolyoxyethylene-18-dimethyl-phosphoric acid ester, a mixture of
  nonylphenol-10-polyoxyethylene-monomethylphosphoric acid ester, and nonylphenol-10-polyoxyethylene-dimethylphosphoric acid ester, hydroxybiphenyl-10-ethoxy-phosphoric acid ester or butyl-mono-4-ethoxy-phosphoric acid ester.

8. A pharmaceutical composition comprising 1 to 95% by weight of a spontaneously dispersible concentrate as claimed in claim 4 and up to 10% by weight of a pharmaceutically acceptable excipient, solvent or stabilizer, wherein the composition is formulated in unit dosage form as micropellets, granules, dragees, suppositories, ampules, or capsules.

9. A spontaneously dispersible concentrate, said concentrate comprising as a coemulgator 0.001 to 50% by weight of a biotenside ester according to one of the formulae (I) to (VII):

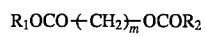 (I)

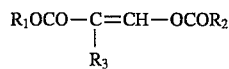 (II)

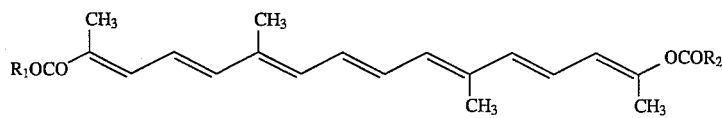 (III)

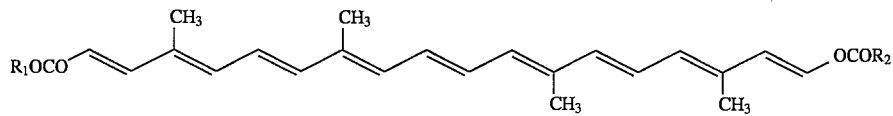 (IV)

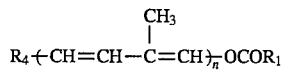 (V)

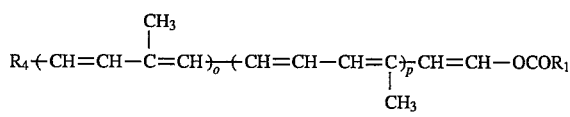 (VI)

 (VII)

or a combination of said biotenside esters of formulae (I) to (VII), wherein

R$_1$ is CITRONELLYL, FARNESYL, GERANYL, PHYTYL, or ISOPHYTYL;

R$_2$ is hydrogen, halogen, C$_{1-4}$ alkyl, CITRONELLYL, FARNESYL, GERANYL, PHYTYL, or ISOPHYTYL;

m is an integer of 1 to 18;

R$_3$ is hydrogen or methyl

R$_5$ is a C$_{5-31}$ alkyl, C$_{5-31}$ alkenyl or C$_{5-31}$ alkapolyene group;

n is an integer of 1 to 5;

o is an integer of 1 to 5;

p is an integer of 1 to 5; and

R$_4$ is a group of one of the following formulae:

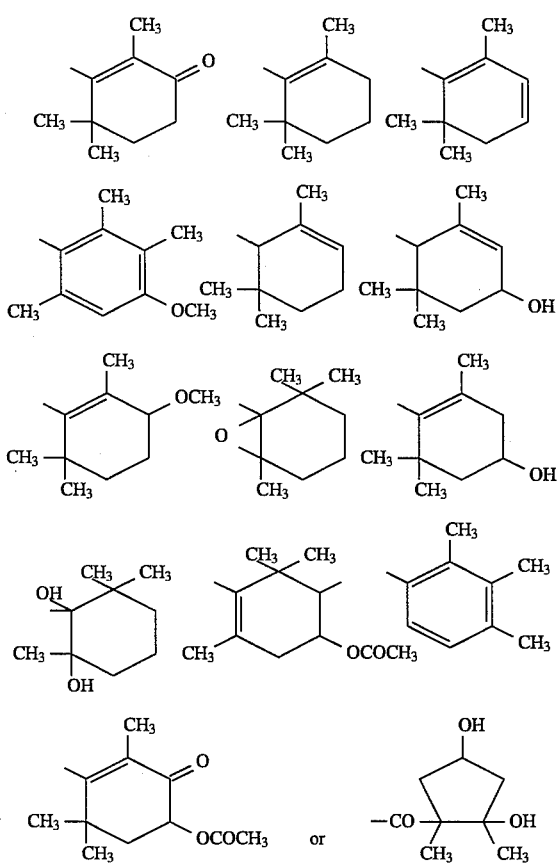

said concentrate further comprising:

0.001 to 30% by weight of a therapeutic agent, a cosmetic agent, or a combination thereof;

0.001 to 90% by weight of a pharmaceutically acceptable tenside or combination of tensides;

up to 10% by weight of a vitamin or provitamin;

up to 10% by weight of a free fatty acid, excipient, diluent, or a combination thereof.

10. A spontaneously dispersible concentrate as claimed in claim 9, wherein the concentrate comprises:

10 to 50% by weight of said biotenside ester or said combination of biotenside esters;

0.5 to 30% by weight of said therapeutic agent, said cosmetic agent, or said combination thereof;

up to 45% by weight of a phosphoric acid ester tenside or a tenside of the formula

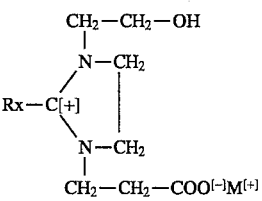

wherein M is hydrogen, an alkali or alkali earth atom, and R$_x$ is a C$_{1-32}$ alkyl or a C$_{2-32}$ alkenyl group, or a multifunctional glucose derivative selected from the group consisting of methyl glucose sesquistearate and PEG-20 methyl glucose sesquistearate; and said concentrate further comprising up to 45% by weight of a pharmaceutically acceptable tert.octyl-phenyl-polyoxyethylene ether having 9 to 10 oxyethylene groups and/or a a fatty acid ester of polyoxyethylene sorbitan.

11. A spontaneously dispersible concentrate as claimed in claim 10, wherein the phosphoric acid ester tenside is a mixture of tristyrylphenolpolyoxyethylene-18-monomethyl-phosphoric acid ester and tristyrylphenolpolyoxyethylene-18-dimethyl-phosphoric acid ester, a mixture of nonylphenol-10-polyoxyethylene-monomethyl-phosphoric acid ester and nonylphenol-10-polyoxyethylene-dimethyl-phosphoric acid ester, hydroxybiphenyl-10-ethoxyphosphoric acid ester or butyl-mono-4-ethoxyphosphoric acid ester.

12. A spontaneously dispersible concentrate as claimed in claim 9, wherein the concentrate comprises:

20% by weight of said biotenside ester or said combination of biotenside esters;

10% by weight of an oily anti-tumor agent;

35% by weight of a pharmaceutically acceptable tert. octylphenylpolyoxy-ethylenether having 9 to 10 oxyethylene groups; and 35% by weight of a phosphoric acid ester tenside or a multi-functional glucose derivative selected from the group consisting of methyl glucose sesquistearate and PEG-20 methyl glucose sesquistearate.

13. A spontaneously dispersible concentrate as claimed in claim 12, wherein the phosphoric acid ester tenside is a mixture of tristyrylphenolpolyoxyethylene-18-monomethyl-phosphoric acid ester tenside and tristyrylphenolpolyoxyethylene-18-dimethyl-phosphoric acid ester tenside or a mixture of nonylphenol-10-polyoxyethylene-monomethyl-phosphoric acid ester and nonylphenol-10-polyoxyethylene-dimethyl-phosphoric acid ester, hydroxybiphenyl-10-ethoxyphosphoric acid ester or butyl-mono-4-ethoxyphosphoric acid ester.

14. A spontaneously dispersible concentrate as claimed in claim 9, wherein the concentrate comprises:

15% by weight of said biotenside ester or said combination of biotenside esters;

0.5 to 30% by weight of a said therapeutic agent, said cosmetic agent, or said combination thereof, up to 40% by weight of a pharmaceutically acceptable tert. octylphenylpolyoxyethylene ether having 9 to 10 oxyethylene groups, and/or a a fatty acid ester of polyoxyethylene sorbitan, and up to 40% by weight of a phosphoric acid ester tenside.

15. A spontaneously dispersible concentrate as claimed in claim 14, wherein the phosphoric acid ester tenside is a mixture of tristyrylphenolpolyoxyethylene-18-monomethyl-phosphoric acid ester tenside and tristyrylphenolpolyoxyethylene-18-dimethyl-phosphoric acid ester tenside or a mixture of nonylphenol-10-polyoxyethylene-monomethyl-phosphoric acid ester and nonylphenol-10-polyoxyethylene-dimethyl-phosphoric acid ester, hydroxybiphenyl-10-ethoxyphosphoric acid ester or butyl-mono-4-ethoxyphosphoric acid ester.

16. A pharmaceutical composition comprising:

1 to 95% by weight of said spontaneously dispersible concentrate as claimed in claim 9; and up to 10% by weight of a pharmaceutically acceptable excipient, solvent or stabilizer;

wherein said concentrate and said excipient, solvent or stabilizer are processed into dosage forms selected from the group consisting of micropellets, granules, coated tablets, tablets, and suppositories.

* * * * *